United States Patent [19]

Mizutani et al.

[11] 4,417,893
[45] Nov. 29, 1983

[54] SANITARY NAPKIN

[75] Inventors: Hiroshi Mizutani; Yoshimi Tsuchiya, both of Yachiyo, Japan

[73] Assignee: Kao Soap Co., Ltd., Tokyo, Japan

[21] Appl. No.: 913,880

[22] Filed: Jun. 8, 1978

[30] Foreign Application Priority Data

Jun. 17, 1977 [JP] Japan .................................. 52-79368

[51] Int. Cl.³ ............................................. A61F 13/16
[52] U.S. Cl. ..................................... 604/366; 604/370
[58] Field of Search ................ 128/284, 287, 290 R, 128/290 W, 296; 604/366–367, 370–372, 378

[56] References Cited

U.S. PATENT DOCUMENTS

| 2,862,251 | 12/1958 | Kalwaites | 128/290 W |
| 3,088,463 | 5/1963 | Harmon | 128/290 W |
| 3,294,091 | 12/1966 | Morse | 128/290 R |
| 3,768,118 | 10/1973 | Ruffo et al. | 128/290 R |
| 3,828,783 | 8/1974 | Kennette et al. | 128/290 W |
| 3,838,694 | 10/1974 | Mesek | 128/290 W |
| 3,886,942 | 6/1975 | Bernardin | 128/290 R |
| 3,934,588 | 1/1976 | Mesek et al. | 128/290 W |
| 4,129,132 | 12/1978 | Butterworth et al. | 128/287 |

Primary Examiner—C. Fred Rosenbaum
Attorney, Agent, or Firm—Flynn, Thiel, Boutell & Tanis

[57] ABSTRACT

A sanitary napkin comprising an absorbent, a liquid-impervious layer covering the bottom, sides and top edge of the absorbent and a non-woven wrapper fabric covering the absorbent and the liquid-impervious layer, wherein the non-woven fabric has a double layer structure comprising a web layer in which most of the fibers are oriented uniformly and another web layer in which the fibers are randomly arranged.

7 Claims, 4 Drawing Figures

SANITARY NAPKIN

BACKGROUND OF THE INVENTION

1. Field of the Invention

The present invention relates to a sanitary napkin for absorbing menstrual discharges.

2. Description of the Prior Art

Conventional sanitary napkins comprise an absorbent in the form of a pad of fluffed pulp, absorbent tissue, absorbent cotton or the like, a liquid-impervious layer convering the bottom, sides and edge portion of the top surface of the absorbent, a thin layer of fibers placed on the top surface of the absorbent, and a non-woven cotton or rayon fabric wrapper covering the assembly. As the non-woven fabric wrapper, there have been used non-woven fabrics made by the wet process and the dry process. The non-woven fabrics made by the wet process have the disadvantages that such fabrics are relatively dense and they are somewhat water-repellent because of the binder that is used therein or because of the hydrophobic fibers that are incorporated therein, whereby their blood absorbency is relatively poor, even when they are subjected to a creping treatment. The non-woven fabrics made by the dry process also have the disadvantages that their surfaces are flat and they are water-repellent because a hydrophobic binder is used therein, whereby their blood absorbency is relatively poor. Therefore, in actual use of conventional sanitary napkins, if the menstrual discharge flow is too fast, the discharge floods and runs off the surface of the napkin to cause unwanted leakage from the sides thereof, rather than being entirely absorbed in the sanitary napkin.

SUMMARY OF THE INVENTION

After intensive investigations, the inventors have found that the above-mentioned disadvantage of conventional sanitary napkins can be overcome by using a non-woven covering fabric having a double layer structure comprising a web layer made of uniformly oriented fibers and a second web layer made of randomly oriented fibers, wherein the two layers are laminated together to form a unitary body. The present invention has been attained on the basis of this discovery.

The present invention provides a sanitary napkin for menstrual discharges comprising a pad of absorbent 3, a liquid-impervious layer 2 covering the entire bottom and sides and the edge portions of the top surface of the absorbent 3 and a non-woven fabric 1 covering the entire assembly, characterized in that the non-woven covering fabric 1 has a double layer structure comprising a first web layer in which most of the fibers are oriented uniformly and a second web layer in which the fibers are randomly arranged.

Figure 1:
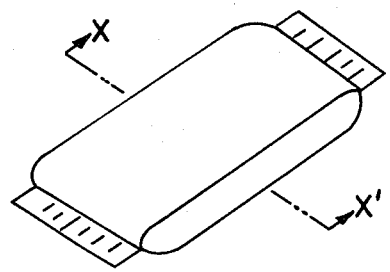
FIG. 1 is a perspective view of a sanitary napkin according to the present invention.
Figure 2:
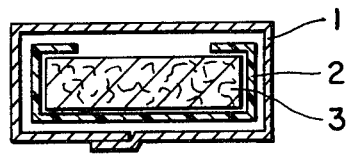
FIG. 2 is a cross section of the napkin taken along the line X—X' in FIG. 1.
Figure 3:
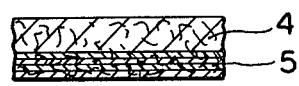
FIGS. 3 and 4 are cross sections of non-woven fabrics of double layer structure according to the present invention.
Figure 4:
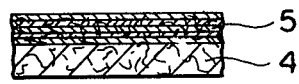

In the sanitary napkin of the present invention, the outer surface of the non-woven fabric 1 (i.e. the surface to be in contact with the skin; the same shall apply hereinafter) can comprise the web layer 4 of random fibers as shown in FIG. 3 or the outer surface can comprise the web layer 5 of uniformly oriented fibers as shown in FIG. 4.

Description will be made first concerning the napkin wherein the outer surface of the non-woven fabric 1 comprises the web layer 4 of randomly oriented fibers. The fibers constituting the outer web layer 4 of random fibers of the non-woven fabric comprise hydrophilic fibers having a high absorbing rate for menstrual discharges and having incorporated therein heat-fusible hydrophobic fibers capable of preventing excessive wetting thereof, whereby to maintain a fluffed bulky condition of the web layer 4 and to adhere to fibers together. For satisfying these requirements, the weight ratio of the hydrophilic fibers to the hydrophobic fibers in the web layer 4 is in the range of from 90/10 to 40/60, preferably in the range of from 80/20 to 50/50. In the fiber structure of the inner web layer 5 of uniformly oriented fibers, the proportion of the hydrophilic fibers relative to the hydrophobic fibers is higher than it is in layer 4 in order to increase the absorbing rate of the layer 5 for menstrual discharges. The weight ratio of the hydrophilic fibers to the hydrophobic fibers in the layer 5 is in the range of from 95/5 to 50/50, preferably in the range of from 90/10 to 60/40. The weight ratio of the random web layer 4 to the oriented web layer 5 is in the range of from 80/20 to 20/80, preferably in the range of from 80/20 to 50/50.

As the hydrophilic fibers, there can be used cellulosic fibers or water-absorbing synthetic resin fibers. As the hydrophobic fibers, there can be used polypropylene fibers and polyethylene-polypropylene conjugately spun fibers. Further, polyacrylic fibers, polyester fibers and polyamide fibers can also be used.

By employing such a non-woven fabric of double layer structure comprising an outer random web layer 4 and an inner oriented web layer 5, excellent sanitary napkins having the advantages described below can be obtained. Since the outer random web layer 4 is bulky, it has a low density and a high void content, thereby exhibiting a high blood-absorbing rate. Consequently, the blood does not run off along the napkin surface, but rather is absorbed readily by the absorbent in the sanitary napkin. Thus, the amount of blood that remains on the surface of the non-woven fabric is very small in quantity, and therefore, the users are not subjected to discomfort. The inner, uniformly oriented web layer 5 acts as a support for the outer random web layer 4. The inner uniformly oriented web layer 5 has a high longitudinal tensile strength which facilitates the preparation of the non-woven fabric and the sanitary napkin and also prevents the non-woven fabric from breaking due to friction or the like during use, even though the outer random web layer 4 having a high bulkiness does not have sufficient strength because adhesion between the fibers thereof is weak. Another advantage of the non-woven fabric is that the feel thereof on the skin is excellent and it is highly shapeable to conform to body contours owing to the soft random web layer 4 on the outer surface.

Now, description will be made about the napkin wherein the outer surface of the non-woven fabric comprises the uniformly oriented web layer (FIG. 4).

In the outer, uniformly oriented web layer 5 in the fiber structure of the non-woven fabric, a mixture of the hydrophilic fibers and the hydrophobic fibers is used in order to reduce the wetting property while maintaining a high absorbing rate. The weight ratio of the hydrophilic fibers to the hydrophobic fibers in the uniformly oriented outer web layer 5 ranges from 90/10 to 40/60, preferably from 80/20 to 50/50. In the inner random web layer 4, the proportion of the hydrophilic fibers is higher in order to maintain a high absorption capacity. Heat-fusible hydrophobic fibers can be incorporated therein, however, in order to impart a durable bulkiness thereto and to adhere the inner layer 4 to the outer, uniformly oriented web layer 5 and also to adhere the fibers in the layer 4 together. The weight ratio of the hydrophilic fibers to the hydrophobic fibers in the layer 4 ranges from 100/0 to 50/50, preferably from 90/10 to 60/40. The weight of the fibers is 10–40 g/m$^2$, preferably 12–30 g/m$^2$. The weight ratio of the outer layer to the inner layer ranges from 20/80 to 80/20.

Although a staple fiber layer is inserted between the non-woven fabric cover and the absorbent in conventional sanitary napkins, such a staple fiber layer is unnecessary when there is used the double layer non-woven fabric of the present invention comprising the outer, uniformly oriented web layer 5 and the inner random web layer 4. The inner random web layer 4 provides the same results as the staple fiber layer. By combining the inner random web layer 4 with the outer uniformly oriented web layer 5 in a unitary body, the strength of the fabric assembly is increased and the thickness and weight of the oriented web layer 5 can be reduced and, in addition, the fiber density is decreased to improve remarkably the absorption of the menstrual discharges on the surface. It has been found that the menstrual discharges rapidly penetrate into the absorbent placed therewithin through the inner random web layer 4, and only a very small quantity of the menstrual discharges remain on the surface, whereby the users are free of any uncomfortable, sticky feeling.

The non-woven fabric is characterized by a high flexibility, a soft pleasant touch on the skin and a very good fitting property to the user's body. As compared with conventional sanitary napkins, the napkins of the present invention can be prepared advantageously by simpler steps, because the staple fiber layer is omitted.

As the absorbent materials suitable for use to form the absorbent layer 3 in the sanitary napkins of the present invention, there can be used fluffed pulp pads, creped tissue and absorbent cotton. Further, hydrophilic synthetic polymer absorbents having a high absorbing capacity can be used together therewith. As the layer 2, there can be used water-proof liquid-impervious tissue which have been subjected to a water-repelling treatment, plastic sheets, laminates of plastic films and papers and polyvinyl alcohol sheets.

The heat-fusible hydrophobic fibers are heat-fused to each other at the points where they are in contact whereby to unite the layers to each other to form a unitary two-layer non-woven fabric. The heat-fused hydrophilic fibers also maintain the structural integrity of the layers and, particularly, maintain the fluffed condition of the random fiber web layer.

The embodiments of the invention in which an exclusive property or privilege is claimed are defined as follows:

1. In a sanitary napkin for menstrual discharges, comprising an absorbent core, a liquid-impervious layer covering the bottom, sides and the edge portion of the top surface of the absorbent core and a non-woven fabric covering the remainder of the top surface of the absorbent core, the improvement which comprises:
said non-woven fabric consists essentially of a unitary laminate of an inner layer disposed adjacent to said absorbent core and an outer layer disposed on the opposite side of said inner layer from said absorbent core, each of said inner and outer layers consisting essentially of a blend of hydrophilic fibers and heat-fusible hydrophobic fibers with said inner layer containing a higher proportion of hydrophilic fibers than said outer layer, one of said inner and outer layers consisting essentially of randomly oriented fibers in a fluffy bulky state, the other of said inner and outer layers consisting essentially of substantially uniformly oriented fibers and having a high longitudinal tensile strength, the hydrophobic fibers of said first and second layers being heat-fused to each other at the locations where they are in contact with each other to unite said first and second layers to each other and to maintain the structural integrity of said first and second layers.

2. A sanitary napkin according to claim 1, wherein the outer layer of the non-woven fabric is said one layer of randomly oriented fibers.

3. A sanitary napkin according to claim 1, wherein the outer layer of the non-woven fabric is said other layer of uniformly oriented fibers.

4. A sanitary napkin as claimed in claim 2, in which the weight ratio of hydrophilic fibers to hydrophobic fibers in said outer layer is from 90/10 to 40/60, the weight ratio of hydrophilic fibers to hydrophobic fibers in said inner layer is from 95/5 to 50/50 and is higher than the corresponding ratio in the outer layer, and the weight ratio of the outer layer to the inner layer is from 80/20 to 20/80.

5. A sanitary napkin as claimed in claim 4, in which the weight ratio of hydrophilic fibers to hydrophobic fibers in said outer layer is from 80/20 to 50/50, the weight ratio of hydrophilic fibers to hydrophobic fibers in said inner layer is from 90/10 to 60/40, and the weight ratio of said outer layer to said inner layer is 80/20 to 50/50.

6. A sanitary napkin as claimed in claim 3, in which the weight ratio of hydrophilic fibers to hydrophobic fibers in said outer layer is from 90/10 to 40/60, the weight ratio of hydrophilic fibers to hydrophobic fibers in said inner layer is from 100/0 to 50/50 and the weight ratio of the outer uniform web layer to the inner random web layer is from 80/20 to 20/80.

7. A sanitary napkin as claimed in claim 6, in which the weight ratio of hydrophilic fibers to hydrophobic fibers in said outer layer is from 80/20 to 50/50 and the weight ratio of hydrophilic fibers to hydrophobic fibers in said inner layer is from 90/10 to 60/40.

* * * * *